United States Patent
Wu

(10) Patent No.: US 6,855,346 B2
(45) Date of Patent: Feb. 15, 2005

(54) PHARMACEUTICAL COMPOSITION HAVING PROPHYLACTIC EFFECTS ON LAMIVUDINE-RELATED DISEASE RELAPSE AND DRUG RESISTANCE AND METHODS OF USING THE SAME

(76) Inventor: Tzu-Sheng Wu, 19F, No. 171, Cheng-Kung Road, Sanchung, Taipei (TW)

( * ) Notice: Subject to any disclaimer, the term of this patent is extended or adjusted under 35 U.S.C. 154(b) by 189 days.

(21) Appl. No.: 10/192,147

(22) Filed: Jul. 11, 2002

(65) Prior Publication Data

US 2003/0147969 A1 Aug. 7, 2003

Related U.S. Application Data

(60) Provisional application No. 60/327,002, filed on Oct. 5, 2001, and provisional application No. 60/331,257, filed on Nov. 13, 2001.

(51) Int. Cl.[7] .......................... A61K 35/78; A61K 35/37
(52) U.S. Cl. ........................ 424/728; 424/725; 424/741; 424/773; 424/777
(58) Field of Search ................................ 424/741, 728, 424/773, 777, 725, 764, 774, 520, 551, 553; 514/893, 894

(56) References Cited

U.S. PATENT DOCUMENTS

| | | | |
|---|---|---|---|
| 5,047,407 A | | 9/1991 | Belleau et al. |
| 6,004,968 A | | 12/1999 | Casey et al. |
| 6,113,920 A | | 9/2000 | Maye et al. |
| 6,288,033 B1 | | 9/2001 | Leung |
| 6,455,078 B1 | * | 9/2002 | Wu .............................. 424/725 |

FOREIGN PATENT DOCUMENTS

WO    WO 00/64427 A2    11/2000

OTHER PUBLICATIONS

Lei et al A one–year trial of lamivudine for chronic hepatitis B. New England Journal of Medicine. 339:61–68. 1998.*

Balzarini, J. et al., Anti–HIV and Anti–HBV Activity and Resistance Profile of 2', 3'–Dideoxy–3'–Thiacytidine (3TC) and its Arylphosphoramidate Derivative CF 1109; Biochemical and Biophysical Research Communications, vol. 225, p. 363–369, 1996.

Lai, C., et al., A One–Year Tiral of Lamivudine for Chronic Hepatitis B; The New England Journal of Medicine, vol. 339, No. 2, p. 61–68, 1998.

Hussain, M. et al., Mutations in the hepatitis B virus polymerase gene associated with antiviral treatment for hepatitis B; Journal of Viral Hepatitis, vol. 6, p. 183–194, 1999.

Liaw, Y. et al., Acute Exacerbation and Hepatitis B Virus Clearance After Emergence of YMDD Motif Mutation During Lamivudine Therapy; Hepatology, vol. 30, No. 2, p. 567–572, 1999.

* cited by examiner

*Primary Examiner*—Herbert J. Lilling
(74) *Attorney, Agent, or Firm*—Fei-Fei Chao; Bingham McCutchen LLP

(57) ABSTRACT

The present invention provides a method for treating patients with liver diseases by co-administrating a pharmaceutical composition and lamivudine to the patients. The pharmaceutical composition is a herbal mixture which contains, as the core ingredients, the aqueous extracts of the entire plant of *Herba Hedyotidis diffusae*, the rhizome of *Rhizoma Bistortae*, the rhizome of *Rhizoma Polygoni Cuspidati*, and the ripe fruit of *Fructus Schisandrae*. The present invention also provides methods for preventing a relapse of hepatitis in patients after the lamivudine treatment has been discontinued and for suppressing the development of lamivudine drug resistance in patients by providing the lamivudine-treated patients with the pharmaceutical composition of the present invention.

15 Claims, 1 Drawing Sheet

PHARMACEUTICAL COMPOSITION HAVING PROPHYLACTIC EFFECTS ON LAMIVUDINE-RELATED DISEASE RELAPSE AND DRUG RESISTANCE AND METHODS OF USING THE SAME

RELATED INVENTION

This application claims the priority of U.S. Provisional Application Ser. No. 60/327,002, filed on Oct. 5, 2001, and 60/331,257, filed on Nov. 13, 2001, which are herein incorporated by reference.

FIELD OF THE INVENTION

The present invention relates to a method for treatment of patients with liver diseases, which includes the administration to patients a drug regimen which contains a pharmaceutical composition and lamivudine. The pharmaceutical composition contains, as the core ingredients, aqueous extracts of the entire plant of *Herba Hedyotidis diffusae*, the rhizome of *Rhizoma Bistortae*, the rhizome of *Rhizoma Polygoni Cuspidati*, and the ripe fruit of *Fructus Schisandrae*. The present invention also relates to methods for prevention of a relapse of liver diseases caused by withdrawal of lamivudine treatment and suppression of the development of lamivudine drug resistance by adminstering to patients the pharmaceutical composition of the present invention.

BACKGROUND OF THE INVENTION

Viral hepatitis is a mostly enterically transmitted liver disease caused by viral infection. The major transmission path of the disease is through ingestion; viral hepatitis is also transmitted through blood transfusion of virus-contaminated blood or blood products such as blood plasma.

Viral hepatitis is widespread around the world. For example, there are approximately thirty million viral hepatitis patients in China including an estimated number of nine million new patients each year and about one hundred million hepatitis B virus (HBV) carriers. Ten percent of the pregnant women in China are estimated to be HBV carriers. About one hundred thousand people in China die each year of liver cancer originated from liver diseases.

HBV infection is caused by hepatitis B virus, which is a 42-nm, double-stranded, and circular deoxyribonucleic acid (DNA) virus belonging to the class of *Hepadnaviridae*. HBV consists of a surface and a core. Four major polypeptide-encoding genes are in the HBV DNA genome: S (surface), C (core), P (polymerase), and X (transcriptional transactivating proteins). The S gene consists of three regions: the pre-S1 region, the pre-S2 region, and the region encoding the surface proteins. The surface proteins constitute the surface antigen (HBsAg). The C gene is divided into two (2) regions, the pre-core and the core region; the C gene encodes two (2) different proteins, the core antigen (HBcAg) and the e antigen (HBeAg).

HBsAg is found on the surface of the virus and produced in excess amount. HBsAg circulates in blood as a 22-nm spherical and tubular particle. HBsAg can be identified in serum 30–60 days after exposure to HBV and persists for variable period of time. Antibody to HBsAg (Anti-HBs) develops after a resolved infection and is responsible for long-term immunity.

Antibody to HBcAg (anti-HBc) develops in all types of HBV infections and persists indefinitely. IgM anti-HBc appears early in infection and persists for equal to or greater than six (6) months, and thus, it is a reliable marker for acute or recent HBV infection.

A third antigen, HBeAg may be detected in samples from patients with either acute or chronic HBV infection. The presence of HBeAg correlates with viral replication and high infectivity. Antibody to HBeAg (anti-HBe) develops in most HBV infections and correlates with the loss of replicating virus and lower infectivity.

Hepatitis B infection progresses with varying outcomes in the patient. Initially, acute infection in the liver causes the body to mount an immune response to get rid of the virus. The immune system tries to clear the virus by destroying HBV infected liver cells. In some people, the immune response succeeds so that the virus along with the infected liver cells are completely destroyed, and the patient makes a complete recovery. This is called the resolution of the disease. In other patients, however, the immune response to the infection is insufficient to get rid of the virus entirely for many months or years or not at all, and the immune response slowly destroys more and more infected liver cells as the virus spreads, which forms long-term infection. This slow but persistent destruction of liver cells by the immune system leads to fibrosis, cirrhosis and even liver cancer. People infected with HBV whose immune systems cannot get rid of the virus are referred to as the chronic HBV carriers. There are usually no obvious physical symptoms in patients of chronic HBV. Specific blood tests will reveal the presence of the virus, and the patient is also contagious via blood, birth, sex, needles, etc. Chronic HBV carriers can pass the virus to others.

U.S. Pat. No. 5,047,407 discloses a chemical compound having antiviral activities. The compound is (2R, cis)-4-amino-1-(2-hydroxmethyl-1,3-oxathiolan-5-yl)-(1H)-pyrimidin-2-one (also known as 3TC), and given the pharmacopoeia name lamivudine and selling in the market under the trade name Epivir by Glaxo SmithKline. Lamivudine is used for treatment and prophylaxis of viral infections.

Lamivudine is a nucleoside analogue that has a potent inhibitory effect on RNA-dependent DNA polymerase of HBV and human immunodeficiency virus (HIV). The antiviral effects of lamivudine on the suppression of HBV replication have been shown in vitro and in vivo. (Lai et al., N. Engl. J. Med. (1998), 339:61–68). Lamivudine accomplishes in most patients the suppression of viral replication as determined by the negativity of serum HBV-DNA, but the compound is much less effective in clearance of HBeAg within a short period of treatment. The ineffectiveness or reduced effect on HBeAg clearance may be attributed to the persistence of HBV covalently closed circular DNA (cccDNA) in hepatocyte nuclei; rapid relapse of HBV replication often occurs after withdrawal of lamivudine treatment. Prolonged lamivudine treatment has been proposed to solve the problem, and the seroconversion rate of HBeAg has been significantly improved.

When lamivudine is used for a prolonged period, it causes selection of lamivudine-resistant mutants of HBV and develops drug-resistance in patients, which casts a new challenge for the treatment regime. (Hussain et al., J. Viral. Hepat. (1999), 6:183–194; Balzarini et al., Biochem. Biophys. Res. Commun. (1996), 2:363–369). Lamivudine-resistant HBV mutants are primarily responsible for acute exacerbation and hepatic decompensation develop in patients during long-term lamivudine therapy. (Liaw et al., Hepatology (1999), 30:567–572).

Once the mutants are present and the patients develop drug-resistance, the physician faces a dilemma whether to stop or continue the treatment. In some cases, continuing treatment results in repeated exacerbation of hepatonecroinflammation, which leads to hepatic decompensation or cirrhosis; on the other hand, stopping treatment may result in re-activation of the wild type virus, which also leads to exacerbation of hepatonecroinflammation. Development of an antiviral treatment regime against the drug-resistance HBV mutants as well as wild type virus is pivotal for such patients.

The present invention provides an herbal pharmaceutical composition that is effective for treating viral infections, particularly, the composition is effective in treating viral hepatitis. The herbal pharmaceutical composition is also effective in treating lamivudine-resistant mutant HBV in vivo and in vitro. Additionally, the herbal pharmaceutical composition enhances the antiviral treatment effects of lamivudine and ameliorates the development of lamivudine-resistant HBV mutants caused by prolonged usage of Lamivudine.

The herbal pharmaceutical composition is named Yi-Gan-Kang (in Chinese, "Yi" means "second or B"; "Gan" means "liver"; "Kang" means "health"; collectively, "Yi-Gan-Kang" denotes "healthy liver devoid of HBV infection"), abbreviated as YGK.

SUMMARY OF THE INVENTION

The present invention provides a method for treating patients with liver diseases by co-administering to said patients a drug regimen which contains an effective amount of a pharmaceutical composition named YGK and lamivudine. YGK contains, as the core ingredients, aqueous extracts of the following herbs: an entire plant of *Herba Hedyotidis diffusae*, a rhizome of *Rhizoma Bistortae*, a rhizome of *Rhizoma Polygoni Cuspidati*, and a ripe fruit of *Fructus Schisandrae*. YGK further contains the aqueous extracts of the following herbs: a rhizome of *Rhizoma Menispermi*, a root of *Radix Scutellariae*, a bovine biliary powder, a tuber of *Radix Curcumae*, a ripe fruit of *Fructus Crataegi*, and a root of *Radix Notoginseng*. Finally, YGK further contains the aqueous extracts of the following herbs: aqueous extracts of a ripe fruit of *Fructus Lycii*, a root of *Radix Ginseng Rubra*, a root of *Radix Scorphulariae*, a root of *Radix Angelicae sinensis*, and a root of *Radix Astragali*. Examples of the aqueous solution for extracting the pharmaceutical ingredients from the herbs include, but are not limited to, water, ethanol, or a mixture thereof. The preferred aqueous solution is water.

YGK can be adminstered to patients orally and/or intravenously. For oral adminstration, the preferred dosage amount is about 0.5 to 5 g of the YGK extract, and most favorably, 1 to 3 g of YGK, per day per person. For intravenous injection, it is preferred that the dosage amount is about 1 to 10 g of YGK, and most favorably 3–5 g of YGK, per day per person. YGK oral dosage form and intravenous injection solution are preferred to give to patients concurrently. The YGK extract is the aqueous extracts of the herbal ingredients after being concentrated. A detailed description of the YGK extract is provided in Example 1 of the "Detailed Description of the Invention," infra.

Lamivudine is preferred to be administered to patients orally. The preferred dosage amount of lamivudine is about 50–500 mg, and most favorably 100–200 mg per day per person.

The co-adminstration of YGK and lamivudine is particularly effective in treating patients with liver diseases such as hepatitis, cirrhosis, and liver cancer. The co-administration of YGK and lamivudine is especially effective in treatment of liver diseases that are caused by hepatitis B viral (HBV) infection.

The present invention also provides a pharmaceutical combination which contains a first dosage unit (i.e., YGK) and a second dosage unit (i.e., lamivudine). YGK is either in an oral dosage form or in an intravenous injection solution. It is preferred that YGK oral dosage dosage form is in the form of capsules. It is preferred to take about 0.1 to 2 g of YGK per adminstration and at about 2–4 times a day. The intravenous injection solution of YGK is at the amount of about 1 to 10 g per administration and preferred to be adminstered to patients once a day.

Lamivudine is preferred to be orally adminstered to patients at about 50 to 500 mg, and most favorably 100–200 mg per administration and at about once a day.

The present invention further provides a method for preventing a relapse of hepatitis in patients after the lamivudine treatment has been discontinued by administering YGK orally and/or intravenously to patients after their lamivudine treatment has been discontinued. This method is particularly effective when the hepatitis is caused by hepatitis B viral (HBV) infection.

Finally, the present invention provides a method for supressing the development of lamivudine drug resistance in patients by adminstering YGK orally and/or intravenously to patients that are taking lamivudine. This method is particularly effective when the lamivudine drug resistance is caused by development of lamivudine-resistant hepatitis B virus (HBV) strains in patients.

DETAILED DESCRIPTION OF THE INVENTION

Figure 1A:
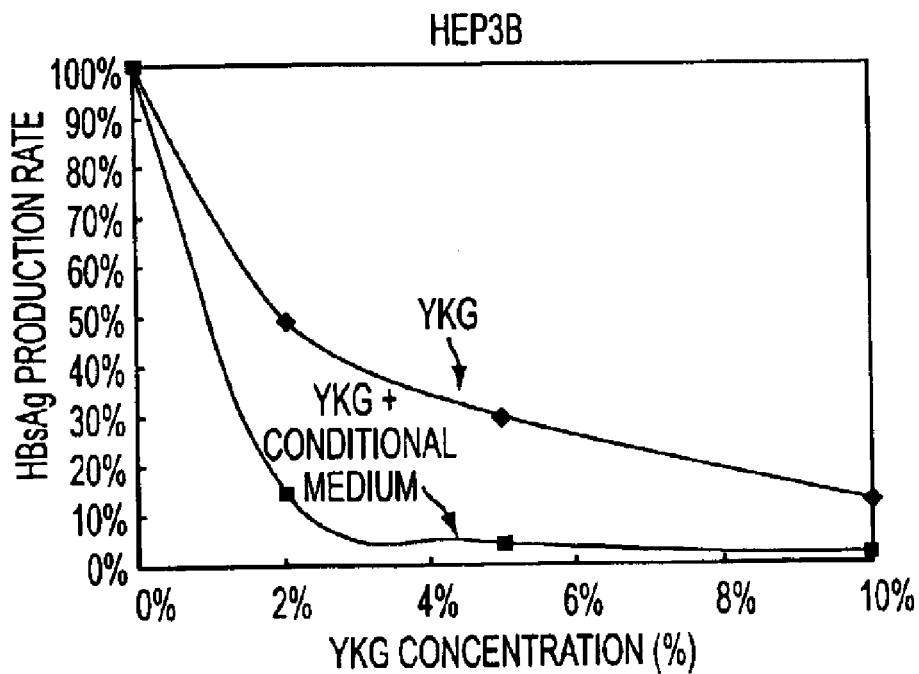
FIG. 1 shows the effects of YGK on the production rate of HBsAg in Hep3B cells (FIG. 1A) and HepA2 cells (FIG. 1B). ♦—♦ represents the cells treated with YGK at different concentrations. ■—■ represents the cells treated with YGK and a "conditional medium". The conditional medium is the medium collected from the culture medium of monocytes which have been incubated for 24 hours.

The lamivudine-resistant viruses have a characteristic amino acid substitution over tyrosine-methionine-aspartate-aspartate (YMDD) motif of the RNA-dependent DNA polymerase, as was seen in lamivudine-resistant immunodeficiency virus. (Balzarini et al., (1996), 2:363–369). The methionine at codon 552 was either replaced by an isoleucine (M552I) or a valine (M552V). (Ling et al., Hepatology (1996), 3:711–713; Tipples et al., Hepatology, 3:714–717; and Naoumov et al., Hepatology (1996), 24:282; which are herein incorporated by reference).

The M552V mutation was frequently accompanied by a leucine528-to-methionine (L528M) substitution. (Fu et al., Biochem. Pharmacol. (1998), 55:1567–1572; Niesters et al., J. Infect. Dis. (1998), 177:1382–1385). These two mutants, M552I and L528M/M552V, were commonly identified lamivudine-resistant mutants. (Liaw et al., Hepatology (1999), 30:567–572). In addition, two additional resistant mutants, L528M/M552V and A529T were developed. Strikingly, replication of some of these mutants was found to be partially lamivudine-dependent.

The pharmaceutical composition of the present invention, YGK, contains fifteen (15) herbs, which are grouped according to their essential roles as follows:

First, there are four (4) herbs which form the core ingredients of YGK. These 4 herbs contributes to the primary efficacy and healing effects of the composition. The 4 herbs are: (1) diffuse hedyotis/spreading hedyotis (Pharmaceutical name: *Herba Hedyotidis diffusae*; Botanical name: *Hedyotis diffusa* Willd.); (2) bistort rhizome (Pharmaceutical name: *Rhizoma Bistortae*; Botanical name: *Polygonum bistorta* L.); (3) giant knotweed rhizome (Pharmaceutical name: *Rhizoma Polygoni Cuspidati*; Botanical name: *Polygonum cuspidatum* Sieb. et Zucc.); and (4) Chinese magnoliavine fruit (Pharmaceutical name: *Fructus Schisandrae Chinensis*; Botanical name: *Schisandra chinensis* (Turcz.) Baill., *S. sphenanthera* Rehd. et Wils.). The preferred weight ratio of diffuse hedyotis, bistort rhizome, giant knotweed rhizome, and Chinese magnoliavine fruit is about 3:3:1:2.

The function of the core herbs function includes clearing heat and toxic substances while improving immune system and circulation, curing symptoms of jaundice, and having beneficial effect on internal organs.

There are six (6) additional herbs that are used to improve and balance the pharmaceutical activities produced by the core ingredients. These six herbs also have toning effect and improve blood circulation in the liver to help the curing of the liver diseases. The six ingredients are: (1) Asiatic moonseed rhizome (Pharmaceutical name: *Rhizoma Menispermi*; Botanical name: *Menisermum dauricum* DC); (2) baical skullcap root (Pharmaceutical name: *Radix Scutellariae*; Botanical name: *Scutellaria baicalensis* Georgi); (3) bovine biliary powder (Zoological name: *Vesica Fellea Bovus*); (4) tumeric root-tuber (Pharmaceutical name: *Radix Curcumae*; Botanical name: *Curcuma wenyujin* Y. H. Lee et C l Ling); (5) Hawthorn Fruit (Pharmaceutical name: *Fructus Crataegi*; Botanical name: *Crataegus pinnatifida* Bge.); and (6) sanqui (Pharmaceutical name: *Radix Notoginseng*; Botanical name: *Panax notoginseng* (Burk.)).

Finally, there are additional five (5) ingredients which are used to primarily provide nutrients and energy sources for patients to expedite the recovery process. These ingredients include: (1) barbary wolfberry fruit (Pharmaceutical name: *Fructus Lycii*; Botanical name: *Lycium barbarum* L.); (2) red ginseng (Pharmaceutical name: *Radix Ginseng Rubra*; Botanical name: *Panax Ginseng* C. A. Mey); (3) figwort root (Pharmaceutical name: *Radix Scrophulariae*; Botanical name: *Scrophularia ningpoensis*); (4) Chinese angelica (Pharmaceutical name: *Radix Angelicae sinensis*; Botanical name: *Angelica sinensis* (Oliv.) Diels); and (5) milkvetch root (Pharmaceutical name: *Radix Astragali*; Botanical name: *Astragalus membranaceus* (Fisch.) Bge.).

Among the five ingredients, red ginseng and milkvetch root also have the capacity of improving immune functions of the body to fense off diseases.

The pharmaceutical names, botanical or zoological names, family names, common descriptions, and major ingredients of the herbs used in the present invention is shown in Table 1.

TABLE 1

Herbs of the Present Pharmaceutical Composition

| Pharmaceutical Name | Botanical/Zoological Name | Family | Common Description | Major Ingredients |
|---|---|---|---|---|
| *Herba Hedyotidis Diffusae* | *Hedyotis diffusa* (Willd.) Roxb., also known as *Oldenlandia diffusa* | Rubiaceae | hedyotis, oldenlandia | hentriacontane, stigmastatrienol, ursolic acid, oleanolic acid, β-sitosterol, ρ-coumaric, β-sitosterol-D-glucoside |
| *Radix et Rhizoma Polygoni Cuspidati* | *Polygonum cuspidatum* Sieb. et Zucc. | Polygonaceae | Giant Knotweed root and Rhizome | emodin, chrysophanol, rheic acid, emodin monomethyl ether, polygonim, and physcion-8-β-D-glucoside |
| *Rhizoma Bistortae* | *Polygonum bistorta* L. | Polygonaceae | Bistort Rhizome | n/a |
| *Rhizoma Menispermi* | *Menispermum dauricum* DC. | Menispermaceae | Asiatic Moonseed Rhizome | n/a |
| *Radix Scutellariae Baicalensis* | *Scutellaria baicalensis* Georgi | Labiatae | Baical Skullcap Root | baicalein, baicalin, wogonin, wogonoside, neobaicalein, oroxylin aglucuronide, camphesterol, β-sitosterol, benzoic acid |
|  | *Vesica Fellea Bovus* |  | Bovine Biliary powder | n/a |
| *Radix Astragali* | *Astragalus membranaceus* (Fisch.) Bge. var. | Leguminosae | Milkvetch Root | D-β-asparagine, 2',4'-dihydroxy-5,6-dimethoxyisoflav |

TABLE 1-continued

Herbs of the Present Pharmaceutical Composition

| Pharmaceutical Name | Botanical/Zoo-logical Name | Family | Common Description | Major Ingredients |
|---|---|---|---|---|
| | mongholicus. (Bge.) Hsiao or Astragalus membranaceus (Fisch.) Bge. | | | ane, calycosin, formononetin, cycloastragenol, astragalosides, choline, betaine, kumatakenin, sucrose, glucoronic acid, β-sitosterol |
| Fructus Lycii | Lycium barbarum L. | Solanaceae | Barbary Wolfberry Fruit | betaine, carotene, physalien, thiamine, riboflavin, vitamin C, β-sitosterol, linoleic acid |
| Radix Notoginseng | Panax noto-ginseng (Burk.) F.H. chen, P. pseudoginseng Wall, P. sanchi Hoo. | Araliaceae | San-chi, notoginseng, Tian qi, Shen sanqi | Arasaponin A, arasaponin B, dencichine |
| Radix Ginseng Rubra | Panax Ginseng C.A. Mey | Araliaceae | Red Ginseng | Panaxatriol, Panaxadiol, Other Panoxisides, Panoquilon, Panaxin, Ginsenin, α-Panaxin, Protopanaxadiol, Protopanaxtriol, Panacene, Panaxynol, Panaenic Acid, Panose, Dammarane, Glucose, Fructose, Maltose, Sucrose, Nicrotinic Acid, Riboflavin, Thiamine |
| Radix Scrophulariae Ningpoensis | Scrophularia ningpoensis Hemsl. or S. buergeriana Miq. | Scrophulariaceae | Figwort Root, Scrophularia | 1-asparagine, oleic acid, linoleic acid, stearic acid, carotene |
| Fructus Schisandrae Chinensis | Schisandra chinensis (Turcz.) Baill., S. sphenanthera Rehd. et Wils. | Magnoliaceae | Chinese Magnoliavine Fruit, schisandra fruit | sesquicarene, β-bisabolene, β-chamigrene, α-ylangene, schizandrin, pseudo-γ-schizandrin, deoxyschizandrin, schizandrol, citral, stigmasterol, vitamin C, vitamin E |
| Tuber Curcumae | Curcuma wenyujin Y. H. Lee et C. Ling., or Curcuma Longa L., or Curcuma aromatica Salisb., or Curcuma zedoaria Rosc., or Curcuma kwangsiensis S. | Zingiberaceae | Turmeric Root-tuber, curcuma | d-camphene, d-camphor, 1-α-curcumene, 1-β-curcumene, curcumin, demethoxycurcumin, bisdemethoxycurcumin, turmerone, ar-turmerone, carvone, ρ- |

TABLE 1-continued

Herbs of the Present Pharmaceutical Composition

| Pharmaceutical Name | Botanical/Zoo-logical Name | Family | Common Description | Major Ingredients |
|---|---|---|---|---|
| | G. Lee et C. F. Liang | | | tolylmethylcarbinoldiferuloylmethane |
| Fructus Crataegi | Crataegus pinnatifida Bge., C. pinnatifida Bge. var. major N.E. Br. or C. suneata Sieb. et Zucc. | Rosaceae | Hawthorn Fruit | crategolic acid, citric acid, tartaric acid, flavone, sugars, glycosides, vitamin C |
| Radix Angelicae Sinensis | Angelica sinensis (Oliv.) Diels | Umbellferae | Chinese Angelica root, tang-kuei | butylidene phthalide, ligustilide, n-butylidene-phthalide, sequiterpenes, carvacrol, dihydrophthalic anhydride, sucrose, vitamin $B_{12}$, carotene, β-sitosterol |

Diffuse hedyotis or spreading hedyotis (*Herba Hedyotidis Diffusae*) belongs to the family of Rubiaceae. The entire plant is used as an herbal medicinal component. The herb has no toxicity. The herb is harvested in summer and autumn in mainland China and in late spring or early winter in Taiwan. In "Materia Medica" (Chinese Herbal medicine), compiled and translated by Dan Bensky & Andrew Gamble, diffuse hedyotidis clears heat and resolves dampness by promoting urination. It is particularly useful for relieving hot painful urinary dysfunction and damp-heat jaundice. Diffuse hedyotidis is the major ingredient in the present herbal pharmaceutical composition which contributes to the medicinal effect on liver diseases and HIV.

Bistort rhizome (*Rhizoma Bistortae*) is the dried rhizome of the plant *Polygonum bistorta* L. It belongs to the family of Polygonaceae. Bistort rhizome has moderate cool property (meaning that bistor rhizome is an "yang" herb). It can be used to remove toxic heat, to promote the subsidence of swelling and to stop bleeding.

Giant knotweed rhizome (*Radix et Rhizoma Polygoni Cuspidati*) is the dried rhizome and root of *polygonum cuspidatum* Sieb. et Zucc. It belongs to the family of Polygonaceae. The plant is grown throughout China, especially Jiangsu, Zhejiang, Anhui, Guangdong, Guangxi, Sichuan, and Guizhou provinces. The plant is harvested in spring and autumn. Giant knotweed rhizome is normally used to dispel damp, to eliminate blood stasis and alleviate pain, to relieve cough, and to resolve phlegm.

Chinese magnoliavine fruit (*Fructus Schisandrae*) is the dried ripe fruit of *Schisandra chinensis* (Turcz.) Baill. or *Schisandra sphenanthera* Rehd. et Wils. It belongs to the family of Magnoliaceae. The former, the best of its kind, is produced in northern parts of China and is habitually called "Northern schisandra fruit"; the latter is commonly referred to as the "Southern schisandra fruit" as it is produced in the southern parts of China. Both kinds can be used for the pharmaceutical preparation of the present invention. The fruit is collected in autumn and dried under the sun after removing the fruit stalks. Chinese magnoliavine fruit is generally used to arrest discharges, replenish qi, promote fluid secretion, tonify the kidney, and induce sedation. Chinese magnoliavine fruit can also decrease the level of GPT (glutamate-pyruvate transaminase) in patients with hepatitis.

Asiatic moonseed rhizome (*Rhizoma Menispermi*) is the dried rhizome of *Menispermum dauricum* DC. It belongs to the family of Menispermaceae. Asiatic moonseed rhizome has cool property. It can be used to remove toxic heat and relieve rheumatic pains.

Baical skullcap root (*Radix Scutellariae*) is the dried root of *Scutellaria baicalensis georgi*. It belongs to the family of Labiatae. The plant is produced in the provinces of Hebei, Shanxi, Inner Mongolia, etc., and collected in spring or autumn. Baical skullcap root is used to remove damp-heat, counteract toxicity, arrest bleeding, and prevent abortion, in patients.

Bovine biliary powder is the gall bladder of the cow, *Vesica Fellea Bovus*. It can clear heat and alleviate spasms.

Turmeric root-tuber (*Radix Curcumae*) is the dried root tuber of *Curcuma wenyujin* Y. H. Lee et C. Ling., or *Curcuma Longa* L., or *Curcuma aromatica* Salisb., or *Curcuma zedoaria* Rosc., or *Curcuma kwangsiensis* S. G. Lee et C. F. Liang. The herb is mainly produced in Sichuan, Zhejiang, Guangdong, and Guangxi provinces in China, and harvested in winter or spring, washed clean after the removal of the hairy rootlets, boiled thoroughly, and dried in the sun. It belongs to the family of Zingiberaceae. Turmeric root-tuber tastes bitter and had cool property. It can be used to clear heat, alleviate spasms and chest pain, and resolve phlegm.

Hawthorn fruit (*Fructus Crataegi*) is the dried ripe fruit of *Crataegus pinnatifida* Bge. var major N. E. Br., or *Crataegus pinnatifida* Bge., or *Crataegus cuneata* Sieb. It is produced primarily in Henan, Jiangsu, and Shandong provinces of China. It is harvested in autumn, sliced, and dried in sunlight. It belongs to the family of Rosaceae. Hawthorn fruit is normally used to stimulate digestion and promote the functional activity of the stomach. It can also improve the normal blood flow and dissipate blood stasis.

Sanqi, or San-chi, (*Radix Notoginseng*) belong to the family of Araliaceae. Sanchi (Sanqi) is the dried root of

*Panax notoginseng* (Burk.) F. H. Chen. The plant is also known as *P. pseudoginseng* Wall and *P. sanchi* Hoo. The plant grows in Yunnan, Guangxi, Sichuan, Guizhou, and Jiangxi provinces of China, and is harvested in the autumn or winter of the third or seventh year, either before the flowers bloom (better) or after the fruit is ripe. H. Gao et al., *Pharmaceutical Research*, (1996) 13(8): 1196–1200, disclose that polysaccharides from *Panax notoginseng* (San-Chi) have immuno-stimulating activities in vitro.

Barbary wolfberry fruit (*Fructus Lycii*) is the dried ripe fruit of *Lycium barbarum* L. It belongs to the family of Solanaceae. The plant is mainly produced in Ningxia, Gansu, and Qinghai provinces of China. It is harvested in summer and autumn. It nourishes and tonifies the liver and kidneys. It can also replenish vital essence and improve eyesight.

Figwort Root (*Radix Scrophulariae*) is the dried root of *Scrophularia ningpoensis* Hemsl. It belongs to the family of Scrophulariaceae. The herb is chiefly produced in Zhejiang and Sichuan provinces of China and harvested in winter when the part of the plant above-ground has withered. The roots are piled and dried in sunlight alternately until the inside becomes black and then sliced for use. Figwort root can reduce heat from blood. It also has nourishing capacity and can counteract toxicity.

Red ginseng (*Radix Ginseng Rubra*) is the steamed and dried root of the cultivated form of *Panax ginseng* C. A. Mey (commonly known as "Yuanshen"). The herb turns red after being steamed and its properties become warmer in nature. It belongs to the family of Araliaceae. The pharmaceutical effects of ginseng are in its dried root. Ginseng has effects on central nervous system. It enhances both stimulatory and inhibitory processes in the central nervous system, thereby improving the adaptability of nervous responses. Ginseng can also lower serum glucose and cholesterol. It also shows therapeutic and preventive effect on peptic ulcer.

Chinese angelica (*Radix Angelicae Sinensis*) is the dried root of *Angelica sinensis* (Oliv.) Diels. It belongs to the family of Umbelliferae. The herb is mainly produced in Gansu and Shanxi provinces of China. It is harvested in late autumn, smoked dry on slow fire after getting rid of the rootlets, sliced, or stir-baked with wine. Chinese angelica can enrich blood, promote blood circulation, regulate menstruation, relieve pain, and relax bowels.

Milkvetch root (*Radix Astragali*) is the dried root of *Astragalus membranaceus* (Fisch.) Bge. var. mongholicus. (Bge.) Hsiao or *Astragalus membranaceus* (Fisch.) Bge. It belongs to the family of Leguminosae. The herb is mainly produced in Shanxi, Gansu, Heilongjiang, and Inner Mongolia of China. The plant of four-year old or older is harvested in spring or autumn. Milkvetch root can promote discharge of pus and the growth of new tissue.

YGK is particularly effective in treating patients with liver diseases. YGK is suitable for preparation in a scale typical for pharmaceutical industry as well as for smaller measure.

In the process for making the herbal composition of the present invention, the individual herbal components are pretreated according to the common procedures. The herbs are cut and put in a container with water and/or lower alcohol (such as ethanol) to boil and simmer twice. The first time of simmering takes about two hours, the solution is collected, and water and/or lower alcohol is added for the second time of simmering for about 1.5 hour. The solutions from the simmering steps are collected by passing through a sieve/filter. The filtrate is then condensed from about 1.4 fold by volume to 1.0 fold by volume. Subsequently, the liquid condensate is spray-dried and granulated to form particles. The particles are further packaged into capsules and preserved for use or for further analysis by the conventional means of the active ingredients to ensure their quality. The liquid condensate can also be made for intravenous injection solution. Approximately 5 ml of intravenous injection solution is in an ampoule.

The composition of the present invention can further be processed and formulated in a form suitable for oral administration or intravenous injection.

In the clinical research on the effects of YGK in treating chronic hepatitis B, the curing effects were valued at:

(1) Continued disappearance of serum HBV-DNA, which is an indication of the clearance of HBV-DNA in serum and liver tissue;

(2) Clearance of HBsAg and production of anti-HBs;

(3) Suppression of HBV replication;

(4) Clearance of HBeAg and production of anti-HBe; and (5) Significant improvement of liver function (as judging by tissue damage) as shown by the normal level of serum aminotransferase, histological examination of dead liver cells, and indications of alleviated inflammation.

When co-administered with lamivudine, YGK is especially effective in curing chronic hepatitis B with quick clearance of serum HBV-DNA and negativity of HBeAg and HBsAg. To be effective for the treatment, YGK is administered into patients in two forms, capsule or intravenous injection solution. It can be administered separately or together with lamivudine. The herbal composition of the present invention has also demonstrated capability of normalizing hepatic enzymes and alleviating clinical symptoms in patients with hepatitis or cirrhosis.

The methods of the present invention are especially effective in curing chronic hepatitis B with quick clearance of serum HBV-DNA and negativity of HBeAg and HBsAg. The method of the present invention for treating hepatitis B includes concurrent- or co-administration of YGK with lamivudine is effective to enhance the anti-viral properties of lamivudine and to suppress the development of lamivudine-resistant HBV mutants caused by prolonged usage of lamivudine.

The combined treatment of YGK and lamivudine of the present invention can achieve the dual goals of suppressing viral replication and improving immune system function of the patient.

Lamivudine, a nucleoside analogue, is effective on the inhibition of enzymatic activity of reverse transcriptase during HBV replication. Six months of lamivudine treatment is effective to decrease HBV-DNA in serum, and the rate of patients turning negative can reach as high as 90.4%. The shortcomings associated with lamivudine treatment are with the cut-off of a single phase in viral replication cycle by lamivudine, the rate for patients turning negative for HBeAg is very low, and a long period of lamivudine treatment is then needed. After the completion of the lamivudine treatment, the patients have a high rate of turning positive for HBeAg.

The two types of YGK formulations, i.e., YGK intravenous injection solution and YGK capsules, have slightly different anti-HBV effects. YGK intravenous injection solution has direct anti-HBV effect. It can block the takeup of nucleotides by the virus during viral replication so that the virus will become feeble and die. YGK capsules, on the other hand, are particularly effective for protecting the liver cells and adjusting the immune function. The combined use of the intravenous injection solution and capsules of YGK is effective for suppression of HBV and recovery of liver function.

The present invention demonstrates that the combined treatment of lamivudine and YGK has multiple functions on multiple phases of HBV replication: Lamivudine inhibits the enzymatic activity of reverse transcriptase during HBV replication, and YGK intravenous injection solution blocks the take-up of nucleotides by the virus during DNA replication; at the same time, YGK capsule adjusts the patient's immune function. The effective combination can quickly clear the serum HBV-DNA within 8 weeks so that 100% of the patients show negative for HBV-DNA, and more patients turn negative for HBeAg after 16 weeks of treatment. Lamivudine treatment in the combined treatment is stopped after 16 weeks of treatment so that the period of taking lamivudine is greatly reduced and the side effects of prolonged lamivudine treatment are avoided including induction of lamivudine-resistant HBV and relapse of the disease.

The following example is illustrative, but not limiting the scope of the present invention. Reasonable variations, such as those occur to reasonable artisan, can be made herein without departing from the scope of the present invention.

EXAMPLE 1

Pharmaceutical Preparation

The kinds and amounts of the herbal ingredients used in the process of making the pharmaceutical composition of the present invention are described in Table 2. The pharmaceutical composition is called "YGK." It can be formulated as injection solution and capsules.

TABLE 2

Ingredients Used In Making YGK Injection Solution and YGK Capsules

| Component | Amount (kg) |
|---|---|
| Diffuse heydyotis | 2.49 |
| Bistort Rhizome | 2.49 |
| Giant Knotweed root and Rhizome | 0.83 |
| Asiatic Moonseed Rhizome | 0.83 |
| Baical Skullcap Root | 0.83 |
| Bovine Biliary powder | 0.083 |
| Milkvetch Root | 1.66 |
| Barbary Wolfberry Fruit | 2.49 |
| Sanchi | 0.83 |
| Red Ginseng | 0.83 |
| Figwort root | 1.66 |
| Chinese Magnoliavine Fruit | 1.66 |
| Turmeric Root-tuber | 0.83 |
| Hawthorn fruit | 1.66 |
| Chinese Angelica | 0.83 |

(1) Quality Controls of Raw Materials

Quality control tests carried out for each individual raw materials according to conventional methods used in the herbal pharmaceutical field which include, but are not limited to, physical appearance, loss on drying, total ash, acid insoluble ash, alcohol extracts, water extracts, TLC, HPLC, heavy metals, microbial counts and residual pesticides. Bovine biliary powder was tested for appearance, TLC and general chemistry.

(2) Manufacturing Process

The individual herbal components were pretreated according to common procedures. The herbs were weighed according to Table 3. A flowchart of the manufacturing process for making YGK capsules and/or injection solution is provided in Table 3:

TABLE 3

YGK Manufacturing Process

| Manufacturing Process | Quality Control Procedure |
|---|---|
| Raw Herbs Delivered | Quality Control of Raw Herbs: Physical Appearance |
| ↓ | |
| Preparation (cutting, drying, etc.) | |
| ↓ | Quality Control of Raw Herbs: Physical Appearance Loss on Drying |
| Obtain Total of 20.003 kg Raw Herbs and Put into Extractor for Manufacturing | Total Ash Acid Insoluble Ash Alcohol Extracts Water Extracts TLC HPLC |
| ↓ | |
| Add 350 L ± 10% Water to Soak Herbs in Extractor for 60 ± 10 min | Heavy Metals Microbial Residues Pesticide Note: Bovine biliary powder (also known as Bovis Bezoar) is only tested for appearance, TLC and General Chemistry |
| ↓ | |
| $1^{st}$ Extraction Parameter Set: | |
| 1. Dial Set Temperature at 95° C. with the Acceptable Range of 90° C.~100° C. | In-Process Quality Control: (take 10~15 g as test sample) Concentration of Solid Content Concentration of Water Content |
| 2. Dial Set Steam Pressure at 2kg/cm2. | |
| 3. Dial Read Out the Lid Pressure at 0.2~0.4 kgf/cm² Range. | |
| 4. Extract for 45 minutes. | |
| ↓ Liquid Extract | |
| $1^{st}$ Concentration Parameter Set: | |
| 1. Dial Read Out Vacuum at −60~ −76 cmHg. | |
| 2. Dial Read Out Temperature at 40° C. ± 5° C. | |
| 3. Process for 40 minutes. | |
| Raw Herbs Add Water 350 L ± 10% | |
| $2^{nd}$ Extraction Parameter Set: | |
| 1. Dial Set Temperature at 95° C. with the Acceptable Range of 90° C.~100° C. | |
| 2. Dial Set Steam Pressure at 2kg/cm². | |

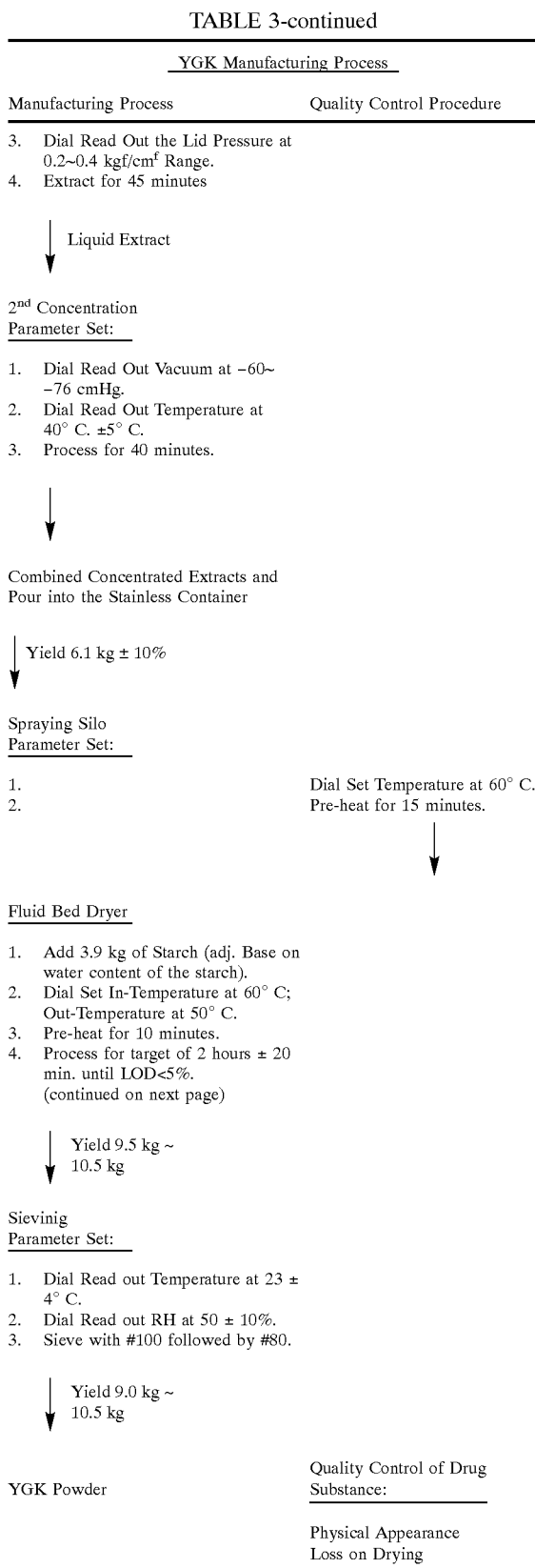

TABLE 3-continued

YGK Manufacturing Process

| Manufacturing Process | Quality Control Procedure |
|---|---|
| | TLC |
| | HPLC |
| | Heavy Metals |
| | Microbial |
| | Residues Pesticide |
| | Stability |

The individual herb was cut into small pieces and thoroughly mixed together. The mixed herbs were placed in bags with sufficient space to spread out. The bags were placed in an extractor with 350 L (±10%) of water and soaked for about 60±10 min. The herbs were first extracted at 95±5° C. under steam pressure of 2 kg/cm$^2$ and lid pressure of 0.2–0.4 kg/cm$^2$ for 45 min. The water extract was collected into a concentrator and concentrated at 40±5° C. under vacuum of −60 to −76 cmHg for 40 min to form the first concentrate.

The herbs in the bags were recovered from the extractor, placed into another 350 L (±10%) of water and extracted again at 95±5° C. under steam pressure of 2 kg/cm$^2$ and lid pressure of 0.2–0.4 kgf/cm$^2$ for 45 min. The extract from the second extraction was collected into a concentrator and concentrated at 40±5° C. under vacuum of −60 to −76 cmhg for 40 min to form the second concentrate.

The first and second concentrates were combined and poured into a stainless container. The total weight of the combined concentrates was about 6.1 kg±10%. The combined concentrates were called the "YGK extract."

For the YGK injection solution, about 0.4 g of the "YGK extract" was dissolved in about 1 ml of the injection buffer. About 5 ml of the injection solution was poured into an ampoule.

For the YGK powders (which were packaged into YGK capsule), about 3.9 kg of starch (adjustable based on the water content of the starch) were added to the YGK extract and spray dried in a fluidized bed setting at in-temperature of 60° C. and out-temperature of 50° C. for approximately 120±20 min until LOD (limit of detection) <5%.

The resultant powders were passed through a 100-mesh sieve and then a 80-mesh sieve. The final yield of the YGK powders were about 9.5~10.5 kg. The YGK powders were further packaged into capsules. There were two dosage forms of YGK capsules: A 500 mg of the YGK capsule, which contained about 305 mg of the "YGK extract" and about 195 mg of starch; and a 220 mg of the YGK capsule, which contained about 134 mg of the "YGK extract" and about 86 mg of starch.

(3) In-process Quality Controls

After the extracts were concentrated, a 10–15 g sample was collected and the concentrations of the solid content and the water content were determined by methods described in US Pharmacopoeia, China Pharmacopoeia, and/or Japanese Pharmacopoeia.

(4) Quality Control of YGK Powders

Quality control tests carried out for the YGK powders include, but are not limited to, physical appearance, loss on drying, total ash, acid insoluble ash, alcohol extracts, water extracts, TLC, HPLC, heavy metals, microbial counts, residual pesticides and stability by conventional methods and by methods described in US Pharmacopoeia, China Pharmacopoeia, and/or Japanese Pharmacopoeia.

(5) Quality Control of YGK Capsules

Quality control tests carried out for the 500 mg YGK capsules include, but are not limited to, physical appearance, loss on drying, total ash, acid insoluble ash, alcohol extracts, water extracts, TLC, HPLC, heavy metals, microbial counts, residual pesticides and stability by conventional methods and by methods described in US Pharmacopoeia, China Pharmacopoeia, and/or Japanese Pharmacopoeia.

EXAMPLE 2

Efficacy of the YGK Herbal Composition on Treatment of Patients with Hepatitis B (HBV)

The clinical research was conducted in the Liberty Military Hospital 211 in China. The course of hepatitis B is determined by many factors, including immune response, host genetic factors, and HBV mutations. The chronic hepatitis distinguishes from the acute hepatitis. The acute hepatitis is the active and symptomatic infection of the liver. A patient with the acute hepatitis is contagious. Symptoms of acute HBV infection are non-specific, but may include malaise, anorexia or jaundice. A chronic hepatitis patient is asymptomatic. The HBV is present in the liver and blood, although there are usually no obvious physical symptoms. Specific blood tests will reveal the presence of the virus, and the patient is also contagious via blood, birth, sex, needles, etc. Cirrhosis is the pathological dysfunctional state of the liver, the hardening of the liver as the result of chronic hepatitis, chronic persistent hepatitis (CPH) and chronic active hepatitis (CAH).

A total of 948 patients with acute HBV, chronic HBV, and liver cirrhosis participated in a clinical comparative study. The patients were divided into two (2) groups. The study group had 642 patients and the comparative group has 306 patients. The data on patients who participated in this study are listed in Table 4.

TABLE 4

Patients Data in the Clinical Study

| Group | Study Group | Comparative Group |
| --- | --- | --- |
| Total Number of Patients | 642 | 306 |
| Sex Distribution of the Patients | Male: 482<br>Female: 160 | Male: 229<br>Female: 77 |
| Age Distribution of Patients | 7 to 74 years old<br>(average age: 32.5) | 8 to 70 years old<br>(average age: 30.5) |
| *Symptoms of Patients' Liver Disease | Acute Hepatitis B: 282<br>Chronic Hepatitis: 276<br>Cirrhosis: 84 | Acute Hepatitis B: 109<br>Chronic Hepatitis B: 114<br>Cirrhosis: 83 |

(*According to the diagnosis criteria of Hepatitis revised at the Shanghai Hepatitis Conference in 1980, Shanghai, China.)

The patients were treated according to the following regime:

(1) The patients in the study group were each orally administered eight (8) YGK herbal composition containing the herbal composition of the present invention per day.

(2) The patients in the comparative group were each orally administered four (4) Hugang ("liver protecting") tablets per day. Hugang (liver-protecting) tablet is made from schisandra fruit (*Fructus Schisandrae Chinensis*) alcohol extractant, liver-protecting extractant (including Junchen, Zihu, and woad root (isatis root, *Radix Isatidis seu Baphicacanthi*)), and biliary powder, etc. It has an effective rate of 95.08% for treating chronic hepatitis (70% with significant effect), and 82.5% for treating cirrhosis (63% with significant effect).

The treatment lasts for ninety (90) days.

Table 5 shows the results of this clinical study.

TABLE 5

Effects of YGK Capsule Treatment

| Group | Number of Patients with Positive Effect* (%) |
| --- | --- |
| Study (642 patients) | 456 (71.03%) |
| Comparative (306 patients) | 104 (33.98%) |

($p < 0.01$)
*Positive effect means that the hepatitis B envelope antigen (HbeAg) and HBV DNA of the patients turn negative after taking the YGK herbal composition for 90 days.

As indicated in Table 5, approximately 71.03% of patients who took the YGK herbal composition for 90 days show positive responses to the herbal composition. This is contrary to the comparative group where the patients were given a popular "liver protecting" tablets which were available in the Chinese market. Patients who had taken the "liver protecting" tablets only have an effective rate of approximately 33.98% to show improvement in their liver diseases.

EXAMPLE 3

Toxicity Study of the YGK Herbal Composition in Animals

Purpose:

The following experiment was conducted at the Toxicology Laboratory of the Institute of Labor, Health, and Occupational Disease of Heilongjiang Province in China to examine acute toxicity of the YGK herbal composition during intravenous injection in animals.

Methods:

Experimental animals were Japanese big-ear white rabbits obtained from the Animal Center of Haerbin Medical University in Haerbin, Heilongjiang Province, China. These rabbits were characterized by the obvious blood vessels on ears which facilitates the operation of injection during the experiments.

Ten (10) rabbits were obtained including six (6) males and four (4) females, each weighing between 1900 g to 3000 g.

The rabbits were randomly divided into two (2) groups, five rabbits in each group including two (2) females and three (3) males. The YGK herbal composition was intravenously injected into the rabbits through the veins on their ears at dosages of 10 g/kg and 15 g/kg, respectively, for two groups.

The concentration of injection fluid containing the herbal composition was about 1 g/ml. So the higher dosage group at 15 g/kg has a concentration of about 15 ml/kg, which could be calibrated as a sixty (60) kg-weighted adult who was treated by 900 ml of the herbal composition at a time.

The rabbits were observed for behaviour continuously for a period of two (2) weeks after intravenous injections. Observation was conducted hourly at day 1; during the following days, observation was conducted four-six (4–6) times per day.

At the end of the observation period, rabbits were sacrificed and dissected to examine the eyes, liver, lung, and spleen for adverse effects.

Results:

No abnormal behavior was observed of the rabbits during the observation period. The rabbits showed normal body weight increase during the period. After the sacrifice and dissection, inspection of the eyes, liver, lung, and spleen showed no extraordinary syndromes. The results when compared to a general acute toxicity index were normal and no acute toxicity.

EXAMPLE 4

In Vitro Anti-viral Activity of YGK

The production of HBsAg by human hepatoma Hep3B cells was very sensitive to various agents. (Hsu et al., J. Biol. Chem. (1993), 268:23093–23097). Thus, Hep3B cells could be developed as an effective assay system for examining antiviral activity associated Chinese herb medicine.

In order to further study the regulation of gene expression and viral replication of HBV, another hepatoma cell line, HepA2, was developed. HepA2 cell was derived from HepG2 cell by transfection of tandem arranged HBV genome into HepG2 cell which contains no HBV sequence in its genome. HepA2 cell could synthesize and secrete both HBsAg and HBeAg into culture medium.

These two cell lines were used as a model system to examine the antiviral activity of YGK. Because YGK has been used to directly treat patient with chronic active hepatitis by i.v. injection, the possibility that YGK could cooperate with cytokines secreted by the monocytes in circulation to inhibit HBsAg production by liver cells was also tested by collecting the culture medium from monocytes (from blood) incubated for 24 h. The monocyte-incubated cultured medium was named as the "conditional medium."

Figure 1B:
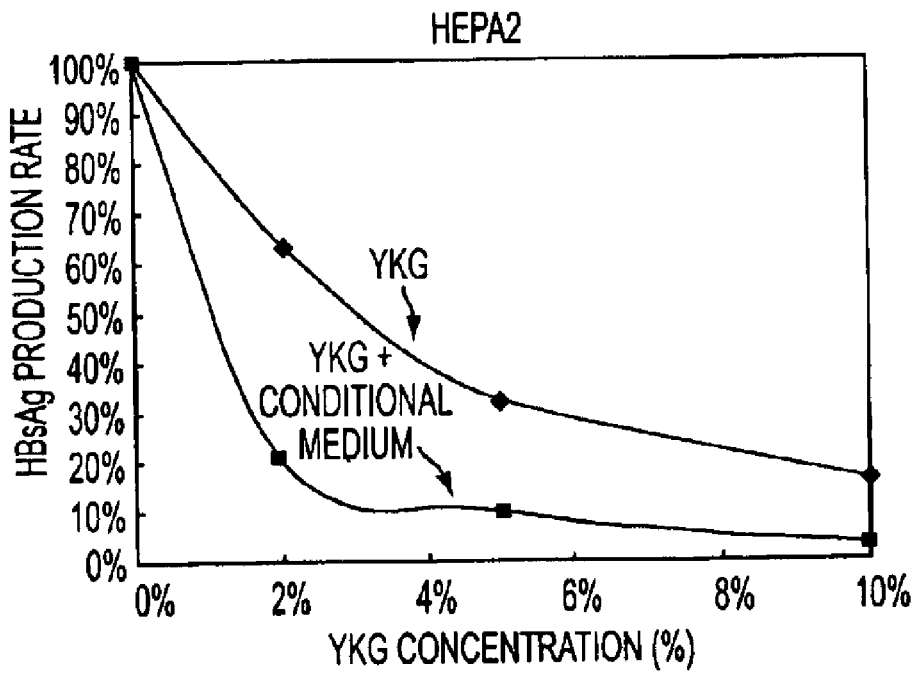

The Hep3B cells and HepA2 cells were then treated with either YGK alone or YGK with the conditional medium. The results are shown in FIG. 1.

The inhibitory effect of YKG alone on HBsAg production in both Hep3B and HepA2 cells was dose dependent. (♦—♦ in FIG. 1A). About 50% of HBsAg production was inhibited in Hep3B cells when YKG was at a concentration of about 2% (w/v). About 50% of HBsAg production were inhibited when YGK was at a concentration of about 3%.

In Hep3B cells, the conditional medium alone has no effect on HBsAg production. (Not shown in FIG. 1A). However, when the conditional medium was added to the culture medium for Hep3B cells, together with 2% of YGK, the production rate of HBsAg in Hep3B cells decreased from about 50% (without the conditional medium) (♦—♦) to about 15% (with the conditional medium). (■—■ of FIG. 1A). The inhibitory effect of HBsAg production appeared to be plateaued at about 4% YGK, where the HBsAg production rate was at about 5%.

In HepA2 cells, the conditional medium alone appeared to have some effect on HBsAg production. (Not shown in FIG. 1B). When the conditional medium was added to the culture medium for Hep3B cells, together with 2% of YGK, the production rate of HBsAg in Hep3B cells decreased from about 65% (without the conditional medium) to about 20% (with the conditional medium). (■—■ of FIG. 1A). The inhibitory effect of HBsAg production appeared to be plateaued at about 3–5% YGK, where the HBsAg production rate was at about 10%.

EXAMPLE 5

In Vitro Anti-Viral Studies of The Effects of YKG on Inhibiting The Viral Replication of lamivudine-resistant HBV Mutants Methods:

(1) Site-Directed Mutagenesis

The methods to generate plasmids containing HBV genomes are according to Yeh et al. (Yeh et al., Hepatology (2000), 31:1318–1326). Briefly, a plasmid, pCMVHBV, was generated by inserting one copy of greater-than-unit-length HBV genome (3.37 kb; nucleotides 1820 to 1990; adw subtype, derived from pECE-C [Walsh et al., Gut (2001), 49:436–440]) into a vector, pRc/CMV (Invitrogen, SanDiego, Calif.). A Hind III site and an Xba I site were engineered at the 3' and 5' ends of this insert.

To generate plasmids expressing lamivudine resistance mutants, site-directed mutagenesis experiments were carried out using a PCR-based strategy. Two primers, Pol-L (upstream) and Pol-R (downstream), which flanked the mutation sites, are synthesized. A set of primers, complementary to each other and spanning the mutation sites, are also synthesized. This set of primers (sense and anti-sense) contained the engineered mismatched nucleotides for site-directed mutagenesis. Two sets of PCR (30 cycles) were carried out using Pol-L/anti-sense and Pol-R/sense primers, respectively, as PCR primers. The resulting DNA fragments were gel-purified. One tenth of each purified DNA fragments were mixed together and another PCR reaction (10 cycles) was performed in the absence of primers. Finally, Pol-L and Pol-R were added to the reaction and 20 more cycles of PCR were performed. After digested with Xba I and purified by agarose gel electrophoresis, the resulting DNA fragment was used to replace the corresponding Xba I to Xba I fragment (nucleotides 250 to 1990) in pCMVHBV. The nucleotide sequences of all primers used in the site-directed mutagenesis experiments were published previously. (Yeh et al., Hepatology (2000), 31:1318–1326).

The plasmids, pCMV-LLTQ and pCMV-YIDD, were constructed by one step of mutagenesis experiment. The other two plasmids, pCMV-YVDD-LMAQ and pCMV-YIDD-LMAQ, in which mutations were located in two separate positions, were constructed by a two-steps mutagenesis experiment. An intermediate plasmid, pCMV-LMAQ, was first generated for the second step of experiment to generate the final plasmids. The nucleotide sequences of all DNA plasmids were verified by DNA sequence analysis.

(2) Transfection of DNA Plasmids into HepG2 Cells

HepG2 cells were maintained in minimal essential medium (MEM) containing 10% fetal bovine serum. The standard $CaPO_4$ precipitation method was used to transfect cells. Cells were glycerol shocked for 1 min at 5 h after transfection. The culture medium was changed on the second day and desirable concentrations of YKG were added. The cells were harvested 24 hrs later.

(3) Isolation of HBVDNA and Southern Blot Analysis

HBV-DNA was analyzed by southern blot. Extraction of HBV DNA from HepG2 cells was carried out according to a previously described protocol with minor modification. (Yeh et al., J. Med. Virol. (1998), 55:42–50). Briefly, cells were trypsinized from the dish, rinsed with phosphate-buffered saline twice and lysed with 0.5 ml of TBS (10 mM Tris-HCl [pH 7.2], 150 mM NaCl) containing 0.5% Nonidet P-40 (NP-40). After a brief centrifugation in a microcentrifuge at 1500×g, the supernatant was transferred to a new tube and adjusted to 10 mmol/L of $MgCl_2$. After digested with 100 μg/mL of DNase I for 30 min at 37° C., ethylene-diaminotetraacetic acid (EDTA) was added to a final concentration of 30 mmol/L to stop the reaction. To extract HBV DNA, an equal volume of buffer containing proteinase K (50 mM Tris-HCl [pH 7.2], 1 mM EDTA, 1% SDS, 0.45% NP-40, and 200 μg/ml protease K) is added and the mixture is incubated for 3 h at 55° C. After two extractions with equal volumes of phenol-chloroform and one extraction with chloroform, the DNA is precipitated with acid ethanol and dissolved in TE buffer (10 mM Tris [pH8.0], 1 mM EDTA).

To detect HBV DNA, the extracted samples were loaded onto a 1% agarose gel for electrophoresis before blotted onto a nitrocellulose membrane. HBV DNA is detected by hybridization with a digoxigenin-labeled probe. The method of labeling the probe as well as the sensitivity, specificity and effective range for quantifying HBV DNA with this probe are described elsewhere.

Result:

The effect of YGK on replication of HBV was assessed by detecting HBV-DNA replication intermediates by electrophoresis followed by southern blot analysis after 24 hours of incubation of HBV incubation in HepG2 cells. The relative amounts of relaxed circular plus linear forms of HBV-DNA were measured by densitometry and the amount of HBV-DNA derived from cells without drug treatment (0 mg/ml of drug) was assigned as 1 fold.

The results show that YGK, at a concentration of 20 mg/ml, inhibited viral replication in widetype HBV (suppressed to 0.61 fold), M552I HBV mutant (suppressed to 0.76 fold), L528M/M552V HBV mutant (suppressed to 0.45 fold), and A529T HBV mutant (suppressed to 0.61 fold).

In sum, it appeared that YGK could effectively suppress replication of most of the lamivudine-resistant HBV mutants.

EXAMPLE 6

Efficacy of YGK and Lamivudine Treatment on Patients with Chronic Hepatitis B (HBV)

The clinical research was conducted in Liuhua Hospital in Shenzhen, China.

Purpose:

The clinical research studied the effects of YGK and Lamivudine treatment, either alone or in combination, on the clearance of serum HBV-DNA and negativity of HBeAg in chronic hepatitis B patients.

Method:

I. Test Articles

YGK injection solution (5 ml/ampoule, containing about 2 g of YGK extract) and YGK capsules (about 220 mg/capsule, containing about 134 mg of YGK extract and about 86 mg of starch) were supplied by Gongming Pharmaceutical Co., Ltd. of Heilongjiang Province, China.

Lamivudine 100 mg tablet was purchased from Glaxo Wellcome.

II. Cases Selection (1) Inclusion Criteria (a) Patients diagnose according to the National Hepatitis B diagnostic standard of 1990.

(b) Serum HBV-DNA continue to be positive 3 weeks prior to treatment.

(c) Serum HBeAg and HBsAg continuously positive and fluctuating or continuous abnormal ALT.

(2) Exclusion Criteria (a) Male or female aging under 18 or over 60, pregnant women or women in lactation.

(b) Patient with cardiovascular, pulmonary, renal or hemophthisis related diseases or mental disorder.

(c) Patient who did not meet the above criteria, did not comply with dosing regimen, or with missing data are excluded.

III. Grouping and Treatment (1) Grouping Method

A total of 135 patients who met the criteria were included in this study. Patients were randomized and divided into group A, B and C. Group A was the treatment group with 48 patients while group B with 42 patients and group C with 45 patients were positive control groups. Patient gender, age, and medical history among groups were statistically analyzed to be insignificant ($p>0.05$) and considered to be comparable.

(2) Treatment Method

Each treatment period lasted for 4 weeks. The duration of treatment was 32 weeks (8 treatment periods).

(a) Group A: Patients received 10 ml YGK injection solution (2 ampoules) diluted with 500 ml 5% glucose by I.V once daily during the first 2 treatment periods; 6 YGK oral capsules (220 mg) three times daily throughout the 8 treatment periods; and 1 lamivudine tablet (100 mg) once daily during the first 4 treatment periods.

(b) Group B: Patients received 1 lamivudine tablet (100 mg) once daily for 8 treatment periods.

(c) Group C: Patients received 10 ml YGK injection solution (2 ampoules) diluted with 500 ml 5% glucose through I.V. once daily during the first 4 treatment periods; and 6 YGK oral capsules three times daily throughout the 8 treatment periods.

IV. Observations and Evaluations (1) Observe Items (a) Hepatitis B biological markers: Serum HBV-DNA, HBeAg, Anti-Hbe, HbsAg, Anti-HBs were analyzed before treatment, at week 4, 8, 16 and 32 during treatment and at week 24 and 48 after treatment termination.

Serum HBV-DNA was measured by polymerase chain reaction (PCR) using 9600 DNA Amplification Machine (PE corp., USA) and reagents from E-li-kang Biotech. Corp., Zhejiang, Wenzhou, China. Serum HBeAg, anti-HBe, HBsAg, and Anti-HBs were determined by the Imx method using Automatic Quick Micro Immune Analytic Instrument and reagents from Abbott Laboratories, USA.

(b) Hepatic functions: ALT was monitored at week 4, 8, 16 and 32 during treatment and at week 24 and 48 after treatment termination.

(c) Adverse effects: Patients were constantly monitored by the medical staff for adverse effect throughout the treatment periods.

(2) Statistical Analysis

Data obtained at weeks 4, 8, 16, and 32 during treatment and at weeks 24 and 48 after treatment termination were analyzed by Chi-square ($X^2$) and t-test. The statistical results obtained were used to evaluate the therapeutic effects.

Results:

1. Observations During Treatment—Serum Biological Markers (1) After One Treatment Period (Four Weeks of Treatment)

The findings after 4 weeks of treatment are shown in Table 6.

TABLE 6

Comparison of Curing Effects after 4 Weeks of Treatment

| Group | Subject Number | ALT (normal) | Clearance of HBV-DNA | Seroconversion of HBeAg | Seroconversion of anti-Hbe | Seroconversion of HBsAg |
|---|---|---|---|---|---|---|
| Group A | 48 | 47 | 46 | 9 | 9 | 2 |
| Group B | 42 | 28** | 0** | 0** | 0** | 0 |
| Group C | 45 | 38* | 16** | 3 | 3 | 0 |

*P < 0.05 comparing with group A
**P < 0.01 comparing with group A

From Table 5, it was obvious that there was significant improvement in patient ALT level after 4 weeks of treatment. 97.9% of Group A patients (47/48) had normal ALT as compared to 66.6% of Group B (28/42, $X^2=15.75$, $p<0.01$) and 84.4% of Group C (38/45, $X^2=5.39$, $p<0.05$). Seroconverison of HBV DNA to negative in group A (95.8%, 46/48) was significantly higher than Group B ($X^2=82.35$, $p<0.01$) and Group C ($X^2=38.04$, $p<0.01$). Seroconversion of HBeAg to negative in group A (18.8%, 9/48) was significantly higher than group B ($X^2=8.55$, $p<0.01$) but not significantly higher than Group C ($X^2=3.07$, $p>0.05$). Seroconversion of HBsAg to negative in Group A was 4.2% (2/48) which was higher but not statistically significant than Groups B and C ($X^2=1.80$ and 1.95, respectively, $p>0.05$). None of the patients in the lamivudine positive control group (Group B) had shown any effect on seroconversion of HBV DNA.

(2) After Two Treatment Periods (Eight Weeks of Treatment)

The findings after 8 weeks of treatment are shown in Table 7.

As shown in Table 7, all patients of Group A had total clearance of HBV DNA while Groups B and C remained unchanged. Seroconversion of HBeAg to negative in Group A patients increased to 37.5% (18/48) which was significantly higher than Group B ($X^2=19.62$, $p<0.01$) but not significantly higher than Group C ($X^2=1.86$, $p>0.05$). Seroconversion of HBsAg to negative in Group A patients increased to 18.7% (9/48) while group B and C did not show any seroconversion, $X^2=8.55$ and 9.39, respectively, with $p<0.01$. None of the patients in the lamivudine positive control group (Group B) had shown any effect on seroconversion of HBV DNA.

(3) After Four Treatment Periods (Sixteen Weeks of Treatment)

Treatment of the YGK injection solution for Group A patients had been discontinued after the $8^{th}$ week. The findings after 16 weeks of treatment are shown in Table 8.

TABLE 7

Comparison of Curing Effects after 8 Weeks of Treatment.

| Group | Subject Number | Clearance of HBV-DNA | Seroconversion of HBeAg | Seroconversion of anti-HBe | Seroconversion of HBsAg | Seroconversion of Anti-HBs |
|---|---|---|---|---|---|---|
| Group A | 48 | 48 | 18 | 18 | 9 | 0 |
| Group B | 42 | 0** | 0** | 0** | 0** | 0 |
| Group C | 45 | 16** | 11 | 11 | 0** | 0 |

**P < 0.01 comparing with group A

TABLE 8

Comparison of Curing Effects after 16 Weeks of Treatment.

| Group | Subject Number | Clearance of HBV-DNA | Seroconversion of HBeAg | Seroconversion of anti-HBe | Seroconversion of HBsAg | Seroconversion of Anti-HBs |
|---|---|---|---|---|---|---|
| Group A | 48 | 48 | 23 | 23 | 18 | 5 |
| Group B | 42 | 26** | 2** | 0** | 0** | 0 |
| Group C | 45 | 36** | 14 | 14 | 0** | 0 |

**P < 0.01 comparing with Group A

As shown in Table 8, it is apparent that the HBV DNA for patients of Group A remained negative even with the discontinuation of the YGK injection solution after the 8$^{th}$ week. For Groups B and C, 61.9% (26/42) and 80% (36/45) of the patients, respectively, had shown negative HBV DNA. However, these remained significantly (p<0.01) lower than that of Group A ($X^2$=22.32 and 10.60, respectively, for Groups B and C). HBeAg seroconversion for Group A had increased to 47.9% (23/48) which was significantly higher than the 4.8% (2/42) of Group B ($X^2$=20.79, p<0.01) but not significantly higher than the 31.1% (14/45) of Group C ($X^2$=2.79, p>0.05). HBsAg seroconversion for Group A had increased to 31.1% (18/48) which was significantly higher than Groups B and C ($X^2$=19.62 and 7.07, respectively, p<0.01). HBV DNA in Group B patients had shown relatively limited seroconversion when compared to Group A.

(4) After Eight Treatment Periods (Thirty-two Weeks of Treatment)

Treatment of the lamivudine tablets for Group A patients and treatment of the YGK injection solution for Group C patients had been discontinued after the 16$^{th}$ week.

higher than Group C ($X^2$=1.95, p>0.05). The results showed that HBV DNA negative seroconversion for Groups A and C was far better than Group B.

2. Adverse Effects

Group A patients had no noticeable side effects associated with the treatment regime except the common soreness at the intravenous injection and dry mouth.

After 16 weeks of treatment, 8 of the 42 patients in Group B showed adverse effects, such as anorexia, abdominal discomfort and fluctuating ALT levels. However, the symptoms disappeared after 2 more weeks of treatment.

After 8 weeks of treatment, 17 of the 45 Group C patients showed dry mouth, abdominal discomfort and fluctuating

TABLE 9

Comparison of Curing Effects after 32 Weeks of Treatment.

| Group | Subject Number | Clearance of HBV-DNA | Seroconversion of HBeAg | Seroconversion of anti-HBe | Seroconversion of HBsAg | Seroconversion of Anti-HBs |
|---|---|---|---|---|---|---|
| Group A | 48 | 48 | 39 | 39 | 24 | 12 |
| Group B | 42 | 38* | 4** | 4** | 1** | 1 |
| Group C | 45 | 42 | 28* | 28* | 16 | 7 |

*P < 0.05 comparing with Group A
**P < 0.01 comparing with group A

As shown in Table 9, it is apparent that at the end of week 32 the patients in Group A continued to be negative for HBV DNA, even though they only took the YGK capsules since the end of week 16. HBV DNA negative conversion for Group B has increased to 90.5% (38/42) which was still significantly lower than Group A ($X^2$=4.77, p<0.05). Group C HBV DNA seroconversion had increased to 93.3% (42/45) which was comparable to Group A ($X^2$=3.35, p>0.05). HBeAg seroconversion for Group A continued to increase to 81.3% (39/48) which was significantly higher than Group B (9.5%, 4/42, $X^2$=46.26, p<0.01) and Group C (62.2%, 28/45, $X^2$=4.19, p<0.05 HBsAg seroconversion for Group A had increased to 50% (24/48) which was significantly higher than Group B ($X^2$=25.38, p<0.01) but not significantly ALT levels. However, the symptoms disappeared after continuation of treatment and the liver function returned to normal.

3. Treatment Follow-up

TABLE 10

Serum biological markers at weeks 24 and 48 after treatment termination.

| Group | Subject Number | Clearance of HBV-DNA | | Seroconversion of HBeAg | | Seroconversion of anti-HBe | | Seroconversion of HBsAg | | Seroconversion of Anti-HBs | |
|---|---|---|---|---|---|---|---|---|---|---|---|
|  |  | 24W | 48W | 24W | 48W | 24W | 48W | 24W | 48W | 24W | 48W |
| Group A | 48 | 48 | 48 | 42 | 42 | 42 | 42 | 29 | 29 | 29 | 29 |
| Group B | 42 | 38* | 26** | 4** | 0** | 4** | 0** | 1** | 0** | 1** | 0** |
| Group C | 45 | 42 | 42 | 32* | 32* | 32* | 32* | 18 | 18 | 11* | 11* |

*P < 0.05 comparing with Group A
**P < 0.01 comparing with Group A

As shown in Table 10, it is apparent that all Group A patients using the combination treatment of YGK injection solution, YGK capsules and lamivudine remained negative of HBV DNA at week 24 and 48 after treatment termination. Three more patients had tested HBeAg negative in addition to the 39 patients tested negative during treatment period, resulting in a 6.2% increase of the seroconversion rate to overall 87.5% (42/48). Five more patients had tested HBsAg negative in addition to the 24 patients tested negative during the 32-week treatment, resulting in a 10.4% increase of the seroconversion rate to overall 60.4% (29/48).

For Group C, no additional HBV DNA seroconversion was observed after the termination of treatment. Four more patients showed HBeAg seroconversion and increased the seroconversion rate by 8.9% to overall 71.1%, however this was still significantly lower than Group A ($X^2=3.91$, $p<0.05$). Two more patients showed HBsAg seroconversion and increased the seroconversion rate by 4.4% to overall 40%, which was not significantly different from Group A ($X^2=3.81$, $p>0.05$).

For Group B, 12 of the 38 patients who were HBV DNA negative during the treatment periods had relapsed and showed positive for HBV DNA at week 48 after treatment termination. Overall seroconversion rate decreased to 61.9% (26/42) which was 28.6% lower than that at the end of the 32-week treatment. Those few patients showing seroconversion of HBeAG and HBsAg at the end of the 32-week treatment had all relapsed to positive at week 48 after termination of treatment.

Conclusion and Discussion:

The curing effects of the treatment regime on chronic hepatitis B are evaluated by continued clearance of HBV-DNA in serum and liver tissue, clearance of HBsAg and production of anti-HBs, suppression of HBV replication, clearance of HBeAg and production of anti-HBe, significant improvement of liver tissue damage as shown by the normal level of serum aminotransferase, histological examination of dead liver cells and indication of alleviated inflammation.

The clearance of HBV and suppression of viral replication are difficult to achieve because of the complicated viral structure and replication cycle of HBV and the close relationship between the condition of the patient's immune system and the existent state of the virus in vivo. Thus, an effective treatment regime for chronic hepatitis B must both attack on every possible stage of the viral replication to block the viral replication and improve the immune system of the patients including breaking the immune tolerance of HBV and adjusting immune balance of the body.

The combined treatment of YGK and lamivudine of the present invention is able to achieve the dual goals of suppressing viral replication and improving immune system function of the patient. Lamivudine, as a representative of the second-generation nucleoside analogue, is very effective on inhibition of the activity of reverse transcriptase during HBV replication. Six-month of lamivudine treatment is effective to decrease HBV-DNA in serum, and the rate of patients turning negative can reach as high as 90.4%. However, there are shortcomings for the lamivudine treatment, i.e., lamivudine only cuts off a single point in the viral replication cycle so that the rate for patients turning negative in HBeAg after lamivudine treatment is very low (9.5%), and a long period of lamivudine treatment is needed. In fact, the present study confirms that the patients treated with lamivudine have a high rate of turning positive in HBeAg after the completion of the treatment.

The two types of YGK formulations, YGK intravenous injection solution and YGK capsules, are effective in treating patients with HBV. YGK intravenous injection solution has direct anti-HBV effect. According to the present ongoing research, YGK intravenous injection solution can block the take-up of nucleotides by the virus during viral replication so that the virus will become feeble and die. YGK capsules, on the other hand, are effective for the protection of liver cells and adjustment of the immune function. The combined use of both the intravenous injection solution and the capsules of YGK can effectively suppress the reproduction of HBV and stimulate the recovery of liver functions.

The combined treatment of lamivudine and YGK has the advantages of providing multiple antiviral functions on multiple phases of HBV replication. First, lamivudine inhibits the enzymatic activity of reverse transcriptase during HBV replication. Second, YGK intravenous injection solution blocks the uptake of nucleotides by the virus during DNA replication. Finally, YGK capsules adjust the body immune function so as to stimulate the recovery of the liver.

The results of the present study demonstrates that the combined treatment of YGK and lamivudine could clear the serum HBV-DNA within 8 weeks. This is based on the facts that 100% of the patients showed negative for HBV-DNA after 8 weeks. The combined use of the two formulation forms of YGK has further implication for developing treatment regime for HBV.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

What is claimed is:

1. A method for treating patients with liver diseases comprising: co-administering to said patients an effective amount of a pharmaceutical composition and lamivudine,
    wherein said pharmaceutical composition comprises aqueous extracts of an entire plant of *Herba Hedyotidis diffusae*, a rhizome of *Rhizoma Bistortae*, a rhizome of *Rhizoma Polygoni Cuspidati*, a ripe fruit of *Fructus Schisandrae*, a rhizome of *Rhizoma Menispermi*, a root of *Radix Scutellariae*, a bovine biliary powder, a tuber of *Radix Curcumae*, a ripe fruit of *Fructus Crataegi*, a root of *Radix Notoginseng*, a rice fruit of *Fructus Lycii*, a root of *Radix Ginseng Rubra*, a root of *Radix Scorphulariae*, a root of *Radix Angelicae sinensis*, and a root of *Radix Astragali*; and
    wherein said pharmaceutical composition prevents a relapse of the liver diseases after lamivudine is discontinued.

2. The method according to claim 1, wherein said pharmaceutical composition is administered to said patients orally.

3. The method according to claim 2, wherein said orally administered pharmaceutical composition is in a dosage amount of about 0.5 to 5 g of said aqueous extracts of said pharmaceutical composition per day per person.

4. The method according to claim 3, wherein said dosage amount of said orally administered pharmaceutical composition is about 1 to 3 g of said aqueous extracts of said pharmaceutical composition per day per person.

5. The method according to claim 1, wherein said pharmaceutical composition is administered by intravenous injection.

6. The method according to claim 5, wherein said pharmaceutical composition is in a dosage amount of about 1 to 10 g of said pharmaceutical composition per day per person.

7. The method according to claim 6, wherein the dosage amount of said pharmaceutical composition is about 3–5 g of said pharmaceutical composition per day per person.

8. The method according to claim 1, wherein said pharmaceutical composition is concurrently administered orally and intravenously.

9. The method according to claim 1, wherein said lamivudine is administered orally.

10. The method according to claim 1, wherein said lamivudine is orally administered in a dosage amount of 50–500 mg per day per person.

11. The method according to claim 10, wherein the dosage amount of said lamivudine is about 100 to 200 mg per day per person.

12. The method according to claim 1, wherein said liver diseases comprises at least one which is selected from the group consisting of hepatitis, cirrhosis, and liver cancer.

13. The method according to claim 1, wherein said liver diseases are caused by hepatitis B viral (HBV) infection.

14. The method according to claim 1, wherein said pharmaceutical composition enhances anti-viral properties of lamivudine.

15. The method according to claim 1, wherein said pharmaceutical composition suppresses development of lamivudine drug resistance.

* * * * *